(12) United States Patent
Pu et al.

(10) Patent No.: US 10,758,492 B2
(45) Date of Patent: Sep. 1, 2020

(54) TWO-DIMENSIONAL POLYMERIC STRUCTURES AND METHOD FOR PRODUCING THEREOF

(71) Applicant: ECOLE POLYTECHNIQUE FÉDÉRALE DE LAUSANNE (EPFL), Lausanne (CH)

(72) Inventors: Ye Pu, Préverenges (CH); Marcin Stefan Zielinski, Lausanne (CH); Demetri Psaltis, Préverenges (CH); Jeffrey Alan Hubbell, Chicago, IL (US)

(73) Assignee: ECOLE POLYTECHNIQUE FÉDÉRALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 15/511,847

(22) PCT Filed: Sep. 15, 2015

(86) PCT No.: PCT/IB2015/057096
§ 371 (c)(1),
(2) Date: Mar. 16, 2017

(87) PCT Pub. No.: WO2016/042484
PCT Pub. Date: Mar. 24, 2016

(65) Prior Publication Data
US 2017/0258737 A1 Sep. 14, 2017

(30) Foreign Application Priority Data
Sep. 16, 2014 (GB) .................. 1416354.7

(51) Int. Cl.
*A61K 9/51* (2006.01)
*A61K 9/50* (2006.01)

(52) U.S. Cl.
CPC ............ *A61K 9/5192* (2013.01); *A61K 9/501* (2013.01); *A61K 9/5115* (2013.01); *Y02A 50/385* (2018.01); *Y02A 50/387* (2018.01); *Y02A 50/465* (2018.01); *Y02A 50/471* (2018.01); *Y02A 50/481* (2018.01)

(58) Field of Classification Search
CPC .... A61K 9/501; A61K 9/5115; A61K 9/5192; Y02A 50/385; Y02A 50/387; Y02A 50/465; Y02A 50/471; Y02A 50/481
See application file for complete search history.

(56) References Cited

U.S. PATENT DOCUMENTS

| | | | |
|---|---|---|---|
| 6,548,264 B1 | 4/2003 | Tan et al. | |
| 2005/0239985 A1 | 10/2005 | Lichtenhan et al. | |
| 2006/0040103 A1* | 2/2006 | Whiteford | B82Y 30/00 428/403 |
| 2010/0280561 A1* | 11/2010 | Song | C08G 63/08 606/86 R |
| 2011/0311635 A1 | 12/2011 | Stucky et al. | |
| 2012/0056341 A1 | 3/2012 | Magdassi et al. | |

FOREIGN PATENT DOCUMENTS

| | | |
|---|---|---|
| EP | 2 335 818 | 6/2011 |
| WO | 2007/112356 A2 | 10/2007 |
| WO | 2008/072239 A2 | 6/2008 |
| WO | 2010/103514 A1 | 9/2010 |

OTHER PUBLICATIONS

Ozcelik et al. (PRL 112, 246803-1 to 246803-5, Jun. 2014). (Year: 2014).*
Bjorkamn et al. (nature/scientific reports 3:3482 pp. 1-7 (2013)) (Year: 2013).*
International Search Report for PCT/IB2015/057096, dated Jan. 15, 2016, 5 pages.
Written Opinion of the ISA for PCT/IB2015/057096, dated Jan. 15, 2016, 6 pages.
Search Report under Section 17 dated Jun. 19, 2015, issued in Patent Application No. GB1416354.7.
Jovanovic, Aleksa V., et al., "Oil Core and Silica Shell Nanocapsules: Toward Controlling the Size and the Ability to Sequester Hydrophobic Compounds," Chemistry of Materials, 2005, vol. 17, No. 13, pp. 3375-3383.
Spernath, L., et al., "Formation of silica nanocapsules from nanoemulsions obtained by the phase inversion temperature method," Micro & Nano Letters, 2010, vol. 5, Iss. 1, pp. 28-36.
Underhill, Royale S., et al., "Oil-Filled Silica Nanocapsules for Lipophilic Drug Uptake: Implications for Drug Detoxification Therapy," Chemistry of Materials, 2002, vol. 14, No. 12, pp. 4919-4925.
Daeneke, Torben, et al., "Wafer-Scale Synthesis of Semiconducting SnO Monolayers from Interfacial Oxide Layers of Metallic Liquid Tin," ACS Nano 2017, vol. 11, pp. 10974-10983.
Grange, Rachel, et al., "Lithium niobate nanowires synthesis, optical properties, and manipulation," Applied Physics Letters, vol. 95, 2009, pp. 143105-1 - 143105-3.
Hsieh, Chia-Lung, et al., "Bioconjugation of barium titanate nanocrystals with immunoglobulin G antibody for second harmonic radiation imaging probes," Biomaterials, vol. 31, 2010, pp. 2272-2277.
Löffler, D., et al., "Growth and Structure of Crystalline Silica Sheet on Ru(0001)," Physical Review Letters, vol. 105, 2010, pp. 146104-1-146104-4.
Pu, Ye, et al., "Nonlinear Optical Properties of Core-Shell Nanocavities for Enhanced Second-Harmonic Generation," Physical Review Letters, vol. 104, 2010, pp. 207402-1-207402-4.
Richardson, Nancy A., et al., "Examining Trends in the Tetravalent Character of Group 14 Elements (C, Si, Ge, Sn, Pb) with Acids and Hydroperoxides," Journal of the American Chemical Society, vol. 121, No. 46, 1999, pp. 10813-10819.
Zielinski, Marcin S., et al., "Hollow Mesoporous Plasmonic Nanoshells for Enhanced Solar Vapor Generation," Nano Letters, vol. 16, 2016, pp. 2159-2167.

* cited by examiner

*Primary Examiner* — Anna R Falkowitz
(74) *Attorney, Agent, or Firm* — Nixon & Vanderhye P.C.

(57) ABSTRACT

The present invention relates to polymeric structures, in the form of flat membrane-like surfaces or micro- nanostructures such as capsules, characterized in that it comprises a substantially two-dimensional layer of covalently-bonded monomers of R-substituted metal or metalloid oxides. Said polymeric structures in most embodiments have a crystal architecture with a hexagonal lattice, but the nature of the covalent bonds present therein impart a bending flexibility that make the polymeric structures behave as a "soft" crystal. Methods of producing such structures, composition comprising thereof and method of using thereof are also included within the present disclosure.

16 Claims, 5 Drawing Sheets

TWO-DIMENSIONAL POLYMERIC STRUCTURES AND METHOD FOR PRODUCING THEREOF

This application is the U.S. national phase of International Application No. PCT/M2015/057096 filed Sept. 15, 2015 which designated the U.S. and claims priority to GB Patent Application No. 1416354.7 filed Sept. 16, 2014, the entire contents of each of which are hereby incorporated by reference.

TECHNICAL FIELD

The present invention generally relates to nanotechnology, material science, and biomedicine. More specifically the invention relates to substantially two-dimensional polymeric structures in the form of flat surface or micro-/nano capsules/spheres, as well as to methods of making and using the same.

BACKGROUND ART

Since the discovery of the fullerenes, carbon nanotubes, and graphene, single-walled materials have attracted rapidly growing interests over the past few decades. Such atomically thin materials possess astonishing properties that are vastly different from the corresponding bulk materials, suggesting a nearly limitless range of applications. Recently, the strong interest also expanded to non-carbon materials, such as boron nitride, molybdenum disulphide, and silicene.

Besides the unusual electronic properties, there is a strong interest in the applications of singled-walled materials, particularly in the delivery of therapeutic agents for medical purposes. For efficient delivery of an agent to the intended target, drug encapsulation and signalled release are crucial to control the drug degradation, overcome the transport barrier, and isolate the harmful side effects. Single-walled material is an optimal choice because of the minimal residue requiring cleaning-up from the body after the release of the drug. However, explorations using fullerenes and carbon nanotubes have focused on the loading of biomolecules on the exterior.

Nanocapsules are a promising new technology for advanced drug delivery. A highly sought-after capability is the controlled drug release from such capsules through external stimuli for pin-point accuracy in diseases therapy, where a thin, impermeable capsule shell that is sensitive to such stimuli is crucial. Techniques to fabricate truly impermeable single-walled capsules with controllable release are still lacking, despite a large body of works in inorganic capsules, liposomes, and polymersomes. A number of release controls were studied, including pH, redox reactions, enzymes, photons, and ultrasound. Ultrasound is particularly versatile and useful means for release control compared to optical and chemical stimuli because of its accurate localization, deep penetration in tissues, local release, and well established safety guidelines. Polymer-based capsules, the vast majority of the techniques studied for this purpose, has not been very effective due to their permeable nature and, where coupled with an ultrasound-based drug release, due to requirement for relatively high acoustic power.

In recent years, hollow silica nanospheres have been developed and used in several areas such as catalysis, imaging or drug controlled release. Preparation of hollow silica nanospheres method is generally performed in two steps, mainly making use of a template, wherein the template material may be a polymer latex, emulsion droplets, inorganic nanoparticles, polymer aggregates or complexes, and surfactant micelles. This multi-step preparation process causes high costs as well as environmental and energy consumption issues; moreover, high temperature calcination and chemical etching to remove the template can damage the core-shell silica, as well as the compounds included in the material.

For instance, CN101121519 describes a technique to fabricate porous hollow silica spheres with a smaller, movable, solid silica sphere core inside. The silica shell has a diameter of 100-1000 nm and a thickness of 20-200 nm with pores of 3-10 nm. The internal silica core is 50-600 nm in diameter. The fabrication procedure include: 1. synthesize the core silica spheres; 2. deposit an organic-inorganic hybrid middle layer on top of the core spheres; 3. coat a porous silica layer outside the middle layer; 4. Etch out the middle layer material to obtain the porous hollow silica spheres with a smaller silica core sphere. Cargo loading was achieved by diffusing drug content through the pores on the shell. The invention further describes an application of extended drug release using the said hollow spheres.

CN102583400 describes a technique to fabricate porous silica hollow spheres with a diameter of 100-1000 nm and a pore size of 2.5-3.5 nm. The procedure involves the ammonia-catalyzed hydrolysis-condensation reaction of tetraethyl orthosilicate (or a similar compound like tetrapropyl orthosilicate) in ethanol (or similar solvent like propanol) with the presence of a surfactant, followed by a calcination step to remove the surfactant component.

WO 2009/023697 describes a method for preparing hollow silica sphere comprising depositing silica-shell precursor on polyamino acid/carboxylate functionalized template particle under neutral condition to give core-shell spheres and removing the template particle by calcination. The method uses commercial polystyrene beads and their amine of carboxylate functionalized derivatives as template or polyamine or polyamino acid template. Hollow silica nanospheres have uniform, stable shell walls with defined porosity and narrow size distribution. The method allows for large scale preparation of the hollow nanoparticles with controlled size of 40 nm to 1 μm. The porosity of the silica shell is convenient for loading and releasing of drugs or used to contain a heavy element (e.g. metal nanoparticle) or magnetic oxides for X-ray or magnetic contrast reagents. The surface of the hollow silica shell is easily functionalized by grafting biofunctional groups that may combine with targeting proteins, antibodies, cells or tissues.

A plethora of other prior art documents including WO 2014/052911, CN103551093, CN103570027A, CN103585938, CN103803565, CN103833040 describe similar compounds and methods for preparing the same. Despite the large amount of work in the field, single layered silica materials, organic or inorganic, arranged in the form of flat surfaces or hollow nanospheres/nanocapsules, possibly having improved features, are needed, as well as rapid and reliable methods for preparing the same.

SUMMARY OF INVENTION

It is the aim of the present invention to provide a polymeric structure, either in the form of micro-/nano structures like capsules/spheres or of a substantially two-dimensional flat layer, having unique features, as well as an efficient method for producing the same. Said method exploits the molecular structure of the monomeric precursors of the invention to create a single layer of molecules in a two-phase solution system. Depending on the physical state of the solution comprising the said two phases (separated phases vs emulsion), the polymeric structure of the invention allows the possibility to create flat molecular layers vs micro- or nanostructures having a hollow fluid core and a single-layered shell.

One objective of the present invention is to provide a polymeric structure, characterized in that it comprises a substantially two-dimensional layer of covalently-bonded monomers of the formula:

wherein

X is a metal or metalloid element selected from the group consisting of Si, Ge, and Sn, and wherein every O atom of a monomer is covalently bonded to an X atom of another monomer.

In a preferred embodiment, the polymeric structure is characterized in that the X—O—X bond angle has a bending flexibility comprised between 120° and 180° with respect to the plane the X atoms lie on.

In a preferred embodiment, the polymeric structure is characterized in that the two-dimensional layer has a crystalline structure.

In one embodiment, the polymeric structure is characterized in that the crystalline structure has a hexagonal lattice in which each of the hexagon edge comprises covalently bonded X—O—X atoms that may occupy different planes.

In one embodiment, the polymeric structure is characterized in that R is an active agent or is functionalized with an active agent.

Another objective of the present invention relates to a hollow micro- or nanostructure, characterized in that it comprises a fluid, non-gaseous inner core and a shell consisting of the polymeric structure as described above.

In one embodiment, the hollow micro- or nanostructure is characterized in that it has a rod-like, round or polygonal shape.

In a particular embodiment, the hollow micro- or nanostructure is characterized in that it is a spherical capsule.

In one embodiment, the hollow micro- or nanostructure is characterized in that the ratio of the two-dimensional portion of the shell vs the total capsule diameter ratio is not less than 1:5.

In one embodiment, the hollow micro- or nanostructure is characterized in that the inner core comprises an active agent.

Another objective of the present invention relates to a method for producing the substantially two-dimensional polymeric structure as previously described, characterized in that it comprises the following step:

a) Providing a biphasic solution consisting of an aqueous solution and an organic phase;

b) adding to said solution amphiphilic condensable monomer precursors of the formula:

wherein

X is a metal or metalloid element selected from the group consisting of Si, Ge, and Sn, R1, R2 and R3 are the same or different condensable moieties and R is a non-polar organic moiety;

c) allowing the deposition and condensation of the monomer precursor on the aqueous solution-organic phase interface; and d) allowing the polymerization process to proceed for a suitable period of time.

In one embodiment, the method is characterized in that the condensable moieties $R_1$, R2 and R3 are OH groups.

In one embodiment, the method is characterized in that the R group is selected from the group consisting of alkyl, allyl, vinyl, alkynyl, phenyl, benzyl, cycloalkyl, hydroxyl, carboxyl, amino or thiol groups.

In one embodiment, the method is characterized in that the aqueous solution and/or the organic phase comprise a polymerization catalyst.

In one embodiment, the method is characterized in that the polymerization catalyst comprises an acid, a base, an organic salt, an inorganic salt, amino acids, polypeptides, enzymes or any combination thereof.

In one embodiment, the method is characterized in that the aqueous solution and/or the organic phase comprise an active agent.

In a preferred embodiment, the method is characterized in that the condensable precursor in step c) is a product of a spontaneous or induced hydrolysis process.

In a preferred embodiment, the method is characterized in that the spontaneous or induced hydrolysis process is performed simultaneously with the condensation process.

In one embodiment, the method is characterized in that step d) further includes a heating process.

In one embodiment, the method is characterized in that the heating process is conducted at a temperature comprised between 40 and 99° C., preferably between 65 and 85° C.

In one embodiment, the method is characterized in that the polymerization process proceeds for at least one hour to several days.

In one embodiment, the method is characterized in that the R group is lately removed.

A further objective of the present invention relates to a method for producing the hollow micro- or nanostructure previously described, characterized in that it comprises the following step:

a) Providing a biphasic solution consisting of an aqueous solution and an organic phase;

b) adding to said emulsion amphiphilic condensable monomer precursors of the formula:

wherein

X is a metal or metalloid element selected from the group consisting of Si, Ge, and Sn;

$R_1$, $R_2$ and $R_3$ are the same or different condensable moieties and R is a non-polar organic moiety;

c) allowing the deposition and condensation of the monomer precursor on the aqueous solution-organic phase interfaces of the emulsion droplets; and d) allowing the polymerization process to proceed for a suitable period of time.

In one embodiment, the method is characterized in that the condensable moieties $R_1$, $R_2$ and $R_3$ are OH groups.

In one embodiment, the method is characterized in that the R group is selected from the group consisting of alkyl, allyl, vinyl, alkynyl, phenyl, benzyl, cycloalkyl, hydroxyl, carboxyl, amino or thiol groups.

In one embodiment, the method is characterized in that the aqueous solution and/or the organic phase comprise a polymerization catalyst.

In one embodiment, the method is characterized in that the polymerization catalyst comprises an acid, a base, an organic salt, an inorganic salt, amino acids, polypeptides, enzymes or any combination thereof.

In one embodiment, the method is characterized in that the aqueous solution and/or the organic phase comprise an active agent.

In a preferred embodiment, the method is characterized in that the condensable precursor in step c) is a product of a spontaneous or induced hydrolysis process.

In a preferred embodiment, the method is characterized in that the spontaneous or induced hydrolysis process is performed simultaneously with the condensation process.

In one embodiment, the method is characterized in that step d) further includes a heating process.

In one embodiment, the method is characterized in that the heating process is brought at a temperature comprised between 40 and 99° C., preferably between 65 and 85° C.

In one embodiment, the method is characterized in that the polymerization process proceeds for at least one hour to several days.

In one embodiment, the method is characterized in that the R group is lately removed.

A further objective of the invention relates to a composition comprising the polymeric structure and/or the hollow micro- or nanostructure as described.

Still a further objective of the invention relates to composition, the polymeric structure and/or the hollow micro- or nanostructure as previously described for use in therapy, prophylaxis or diagnosis of diseases.

Still a further objective of the invention relates to composition, the polymeric structure and/or the hollow micro- or nanostructure as previously described for use as ion-selective transport membrane.

Still a further objective of the invention relates to composition, the polymeric structure and/or the hollow micro- or nanostructure as previously described for use as molecular size-selective transport membrane.

A particular aspect of the invention relies in a method to prepare trisilanol monomer precursors containing no hydrochloride by-product for making $SiO_2$ micro- or nanocapsules, the method comprising the steps of: 1) homogeneously disperse no more than 0.15% by volume of water in a mixture consisting of no less than 30% by volume of a low-boiling temperature, polar aprotic or protic organic solvent, no more than 3% by volume of a fatty alcohol, and a nonpolar solvent for the rest of the volume; 2) dissolve an organotrichlorosilane in a molar amount of three times as much the molar amount of the said water content in 1 mL of the said nonpolar solvent; 3) disperse the later mixture to the former mixture and let the reaction proceed for at least 10 seconds; 4) heat the mixture solution near the boiling temperature for at least 30 minutes to remove the hydrochloride by-product and the low-boiling temperature polar organic solvent.

DETAILED DESCRIPTION OF THE INVENTION

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a," "and," and "the" include plural referents unless the context clearly dictates otherwise. Thus, for example, reference to "a nanocapsule" includes a plurality of such nanocapsules and reference to "a catalyst" includes reference to one or more catalysts, and so forth. Moreover, in the frame of the present disclosure, the terms "nanocapsule", "nanosphere" and " nanostructure" can be used interchangeably, unless otherwise specified.

Also, the use of "or" means "and/or" unless stated otherwise. Similarly, "comprise," "comprises," "comprising", "include," "includes," and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

In the frame of the present disclosure, for "polymeric structure" is herein meant a material substantially consisting of a polymer, a large molecule composed of many repeated smaller units, or subunits, called monomers, tightly bonded together by covalent bonds. The polymeric structure according to the invention is a so called "single layered membrane", a substantially two-dimensional layer of covalently-bonded monomers. The term "membrane" is used herein to implicitly refer to some of the functional aspects of the polymeric structure of the invention, that are intimately linked to its structure. In fact, the polymeric structure disclosed herein behave as a soft barrier when placed between two fluid phases, results selectively permeable to certain molecules while substantially impermeable to others, is sensible to certain physico-chemical external stimuli and the like.

The monomers of the polymeric structure have the formula wherein

X is a metal or metalloid element selected from the group consisting of Si, Ge, and Sn, and wherein every O atom of a monomer is covalently bonded to an X atom of another monomer.

As will be evident for a person skilled in the art from the above definition, the polymeric structure is substantially composed of a two-dimensional, single layer network of R-substituted metal or metalloid oxides, wherein the R groups lie substantially perpendicularly compared to the Euclidean plane the X (metal or metalloid) atoms lie on. In fact, due to the very nature of the metal or metalloid elements, the monomer described above has a tetrahedral molecular structure, with the X atom having an sp3 hybridization and bond angles of 109.5°.

A "metalloid" is a chemical element that has properties in between those of metals and non-metals. In the most preferred embodiment according to the invention, the X atom is silicon. It is understood that the polymeric structure according to the invention can comprise any combination of monomers having different X atoms.

As used herein, a "two-dimensional" polymer is a sheet-like macromolecule consisting of laterally connected repeat units with end groups along all edges (the monomers), wherein the sheet has a thickness in the order of a single molecule (monomolecular). The most known example of a two-dimensional polymer is graphene, an individual layer or sheet of graphite. However, differently to graphene, the polymeric structure of the invention have an R group that can even be, in some embodiments, in the order of several nanometers. Therefore, it is herein understood that the two-dimensional sheet layer of the polymeric structure refers to the film composed of the metal or metalloid oxides (O—X—O), not considering the R group.

The two-dimensional polymeric structure of the invention can show an amorphous, semicrystalline or crystalline topology. In preferred embodiments of the invention, however, the two-dimensional layer of the polymeric structures has a crystal architecture based on a hexagonal lattice in which each of the hexagon edge is composed of the covalently bonded X—O—X atoms that may occupy different planes; in other words, the crystalline structure is made up from regularly tessellated hexagons units repeated in two dimensions, that result in a non-planar honeycomb two-dimensional structure. However, the polymeric structure can have in some circumstances an amorphous appearance, wherein the amorphousness originates from a random deviation of each X and O atoms in a perfect crystalline structure.

One of the key features of the polymeric structure of the invention relies in its flexibility, notwithstanding, in some embodiments, its crystalline nature. As determined theoretically and verified experimentally by the inventors, the X—O—X bonds show a flexibility in terms of bending comprised between 120° and 180° with respect to the plane the X atoms lie on, that is, a Euclidean plane passing through at least two X atoms of the polymeric structure.

The R group can be any kind of chemical group. For instance, in some embodiments the R group can comprise a hydrogen, a hydroxide, aliphatic groups, straight or branched, substituted or not, saturated or not, cyclic or not, or aromatic groups, substituted or not, including but not limited to alkyl groups such as methyl, ethyl, propyl, butyl, hexyl, heptyl, octyl, nonyl, decyl, dodecyl, hexadecyl, octadecyl, and the like; alkenyl groups such as ethenyl, propenyl, n-butenyl, i-butenyl, 3-methylbut-2-enyl, pentenyl, hexenyl, heptenyl, octenyl, cyclohexylbutenyl, decenyl, dodecenyl, hexadecenyl, octadecenyl, and the like; alkynyl groups such as ethynyl, propynyl, n-butynyl, 2-butynyl, 3-methylbutynyl, n-pentynyl, hexynyl, heptynyl, octynyl, decynyl, dodecynyl, hexadecynyl, octadecynyl, and the like; hydroxyl groups such as hydroxymethyl, hydroxyethyl, hydroxypropyl, hydroxybutyl, hydroxypentyl, hydroxyhexyl, hydroxyheptyl, hydroxyoctyl, hydroxydecyl, hydroxydodecyl, hydroxyhexadecyl, hydroxyoctadecyl, and the like; carboxyl groups such as methanoic acid, ethanoic acid, propanoic acid, butanoic acid, pentanoic acid, hexanoic acid, heptanoic acid, octanoic acid, decanoic acid, dodecanoic acid, hexadecanoic acid, octadecanoic acid, and the like; acyl groups such as formyl, acetyl, propanoyl, 2-methylpropanoyl, butanoyl, palmitoyl, acryloyl, propynoyl, cyclohexylcarbonyl, and the like; acyloxy groups such as acetoxy and propionyloxy; alkenyloxyl groups such as allyloxy, 3-butenyloxy, and the like; alkoxy groups such as methoxy, ethoxy, n-propoxy, i-propoxy, n-butoxy, heptoxy, and the like; alkoxycarbonyl groups such as methoxycarbonyl, ethoxycarbonyl, t-butyloxycarbonyl, and the like; thiol groups such as methanethiol, ethanethiol, propanethiol, butanethiol, pentanethoil, hexanethiol, heptanethiol, octanethiol, decanethiol, dodecanethiol, hexadecanethiol, octadecanethiol, and the like; sulfonyl group such as methanesulfonic acid, ethanesulfonic acid, propanesulfonic acid, butanesulfonic acid, pentanesulfonic acid, hexanesulfonic acid, heptanesulfonic acid, octanesulfonic acid, decanesulfonic acid, dodecanesulfonic acid, hexadecanesulfonic acid, octadecanesulfonic acid, and the like; alkyl-SO-moieties; alkyl-$SO_2$-moieties; phosphonic and phosphoric acid groups; primary, secondary, or tertiary amino groups such as aminomethyl, aminoethyl, aminopropyl, aminobutyl, aminopentyl, aminohexyl, aminoheptyl, aminooctyl, aminodecyl, aminododecyl, aminohexadecyl, aminooctadecyl, and the like; aromatic groups such as phenyl, benzyl, halo substituted phenyl, azaheteroaryl, and the like; aroyl groups such as benzoyl, 1- and 2-naphthoyl, and the like; aryl groups such as phenyl or naphthyl, or phenyl substituted or naphthyl substituted; aryloxy moieties; aryloxycarbonyl groups such as phenoxycarbonyl and naphthoxycarbonyl; aryl-SO-moieties; aryl-S-moieties; carboxy moieties; monocyclic or multicyclic cycloalkenyl groups such as cyclopentenyl, cyclohexenyl, cycloheptenyl, norbornylenyl and the like; monocyclic cycloalkyl or multicyclic groups such as cyclopentyl, cyclohexyl, cycloheptyl, 1-decalin, norbornyl, adamant-(1- or 2-)yl, and the like; cyclyloxy groups such as cyclopentyloxy, cyclohexyloxy, quinuclidyloxy, pentamethylenesulfideoxy, tetrahydropyranyloxy and the like; cyclyloxycarbonyl moieties; cyclylsulfinyl moieties; cyclylsulfonyl moieties; cyclylthio moieties; Halo groups such as fluoro, chloro, bromo, or iodo groups; heteroaroyl groups such as thiophenoyl, nicotinoyl, pyrrol-2-ylcarbonyl, 1-and 2-naphthoyl, pyridinoyl, and the like; heteroaryl and substituted heteroaryl groups such as pyrazinyl, thienyl, isothiazolyl, oxazolyl, pyrazolyl, furazanyl, pyrrolyl, 1,2,4-thiadiazolyl, pyridazinyl, benzimidazolyl, benzothienyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, thiazolyl and the like; amino acids; oligopeptidyl groups and so forth.

The R group can be functionalized with active agents or be an active agent itself. The term "functionalized" is meant to include attaching or otherwise coupling said active agent to a portion of the R group and/or in the place of the R group by covalent bonds, non-covalent bonds/interactions or both. In the frame of the present disclosure, an "active agent" is any agent capable of altering, modifying or otherwise interacting with the surrounding environment once brought into direct or indirect contact with it. An active agent can be any agent having the ability to bring about chemical reactions or physical state changes. Suitable agents to be used in the frame of the present invention are for instance imaging or contrast agents, bioactive agents, magnetically or optically active substances, organic compounds, inorganic compounds and/or elements (such as e.g., gold particles).

A "bioactive agent", as well as "bioactive molecule", "bioactive compound", or "therapeutic agent", is any active agent that is biologically active, i.e. having an effect upon a living organism, tissue, or cell. The expression is used herein to refer to a compound or entity that alters, inhibits, activates, or otherwise affects biological or chemical events. Bioactive compounds according to the present disclosure can be small molecules or macromolecules, including recombinant ones. One skilled in the art will appreciate that a variety of bioactive compounds can be used depending upon the needs, e.g. a condition to be treated when the polymeric structure of the invention is intended for prophylactic, therapeutic or even diagnostic purposes. A non-exhaustive list of suitable bioactive agents includes pharmacologically active substances, drugs such as antibiotics or chemotherapeutics, peptides, enzymes, antibodies, vitamins, pesticides, and the like.

Exemplary therapeutic agents further include, but are not limited to, a growth factor, a protein, a peptide, an enzyme, an antibody or any derivative thereof (such as e.g. multivalent antibodies, multispecific antibodies, scFvs, bivalent or trivalent scFvs, triabodies, minibodies, nanobodies, diabodies etc.), an antigen, any type of nucleic acid, such as e.g. DNA, RNA, siRNA, miRNA and the like, a hormone, an anti-inflammatory agent, an anti-viral agent, an anti-bacterial agent, a cytokine, a transmembrane receptor, a protein receptor, a serum protein, an adhesion molecule, a lypidic molecule, a neurotransmitter, a morphogenetic protein, a differentiation factor, an analgesic, organic molecules, polysaccharides, a matrix protein, a cell, and any functional fragment or derivative of the above, as well as any combinations thereof. A "functional fragment" is herein meant any portion of an active agent able to exert its physiological/pharmacological activity. For example, a functional fragment of an antibody could be an Fc region, an Fv region, a Fab/F(ab')/F(ab')$_2$ region and so forth.

In an aspect of the invention, the polymeric structure is not provided in the form of a flat surface (a membrane) but is implemented as the shell of a core-shell micro- nanostructure having, in some embodiments, a rod-like, a generally round or a polygonal shape. In a particular, preferred embodiment, the nanostructure is a substantially spherical micro-nanocapsule. Said structures are characterized in that they are hollow in their inner core, and comprise in said core a fluid, non-gaseous material.

"Nanocapsules" are vesicular systems that are made up of a polymeric membrane which encapsulates an inner fluid core at the nanoscale level. Nanocapsules have a myriad of uses, which include medical promising applications for drug delivery, food enhancement, nutraceuticals, and for the self-healing of materials. The benefits of encapsulation methods are for protection of these substances to protect in the adverse environment, for controlled release, and for precision targeting. They can improve the stability of active substances and can be biocompatible with tissue and cells when synthesized from materials that are either biocompatible or biodegradable. Other advantages of nanometric encapsulated systems as active substance carriers include for instance high substance encapsulation efficiency due to optimized substance solubility in the core, or polymeric shell protection of the inner core against degradation factors like pH and light. A skilled person will appreciate that the present disclosure is meant to include vescicular and micellar core-shell structures such as microcapsules or microspheres, i.e. hollow core-shell structures in a micrometric scale rather than in a nanometric scale. The capsules' size can be tailored based on specific needs by, e.g., reducing or augmenting the inner core fluid content or by altering the condition for producing them, such as e.g. by modifying the concentration of starting materials.

The inner core of micro- or nanostructures comprises a non-gaseous fluid material. Such fluid material comprises liquids such as e.g. aqueous solutions or non-polar solutions, gel-like materials, composite hydrogels and the like. An "aqueous solution" is a solution in which the solvent is substantially made of water. In the frame of the present disclosure, the term "aqueous" means pertaining to, related to, similar to, or dissolved in water. The expression aqueous solution in the frame of the present disclosure also includes highly concentrated and/or viscous solutions such as for instance hydrogels, syrups (i.e., saturated water/sugars solutions) and the like, in which the water content is e.g. less than 5% weight of the total solution weight. A "non-polar solution" is a solution in which the solvent is a non-polar compound. Non-polar solvents are intended to be compounds having low dielectric constants and that are not miscible with water. Non-polar solutions can comprise for example solutions comprising oils, benzene, carbon tetrachloride, diethyl ether, xylene, toluene, isooctane, ethanol, heptanol, cyclohexane, hexadecane, n-octane and the like. An "oil" is any non-polar chemical substance that is a viscous liquid at ambient temperatures and is both hydrophobic and lipophilic. In the frame of the present disclosure, aqueous solutions are also referred to as "water phase" or "polar phase" and non-polar solutions are also referred to as "oil phase" or "organic phase". A fluid material is also intended to comprise any fluid material comprising a gas dispersed within, such as e.g. liquid-gas solutions, and is not intended to comprise gas-only fluids.

Hollow micro- or nanostructures according to the invention offer the possibility of including within the inner core an active agent as the ones previously described. This is of particular interest for what concerns their application, such as e.g. biomedical ones.

Similarly to the flat polymeric structures, the nanostructures of the present invention can be further functionalized. The term "functionalized" is herein meant to include attaching or otherwise coupling functional groups and/or active agents to the inner or outer surface of the shell of a nanostructure of the disclosure. The surface of the micro-nanocapsules shell could be easily functionalized by grafting functional molecular groups or active agents, directly or indirectly, to the monomer units through the R groups, which may combine, for instance, with target proteins, antibodies, cells, or tissues. Beyond biomedical applications, the micro- or nanocapsules of the present invention can be conveniently used as micro/nanoreactors. By functionalizing the shell surface with certain type of catalysts, they can be suitably used for particular applications such as solar hydrogen production or waste water processing. In this latter case, the micro- or nanostructures are ideal ones because of their ability to float on water for a long time period without settling.

Moreover, the outer and inner surface of said shell could also be differentially functionalized. For instance, by functionalizing the inner side of the shell (i.e., the side in direct contact with the inner core of the nanostructure) one could be able to e.g. stabilize the structure, or allow the correct functioning, of the content of the inner core, particularly in case where this latter comprises a payload such as for instance a bioactive agent. By functionalizing the outer side of the shell (i.e., the side of the nanostructure in direct contact with the external environment) one could be able to target, for example, the micro-nanostructures to sites of interest, such as e.g. particular body locations when the technology is applied in the biomedical field. Particularly suitable functional groups for this purpose are for instance natural or modified antibodies or any fragments thereof, integrins, cellular matrix proteins, glycosaminoglycans, bisphosphonates, hydrophobic moieties, natural or modified nucleic acids and the like.

In one embodiment, the hollow micro- or nanostructure is characterized in that the ratio of the two-dimensional portion of the shell vs the total capsule diameter ratio is not less than 1:5.

Methods for producing the flat membrane polymeric structure or the hollow micro- or nanostructure of the invention are also included in the present disclosure. The method for producing a flat substantially two-dimensional polymeric membrane is characterized in that it comprises the steps of:

a) Providing a biphasic solution consisting of an aqueous solution and an organic phase;

b) adding to said solution amphiphilic condensable monomer precursors of the formula:

wherein

X is a metal or metalloid element selected from the group consisting of Si, Ge, and Sn, $R_1$, $R_2$ and $R_3$ are the same or different condensable moieties and R is a non-polar organic moiety;

c) allowing the deposition and condensation of the monomer precursors on the aqueous solution-organic phase interface; and d) allowing the polymerization process to proceed for a suitable period of time.

A "biphasic solution" as used herein is a solution in which a nonpolar solution as defined above is added to an aqueous solution so that the two phases reside in separated layers and form an interface. An "amphiphilic" molecule is a chemical compound possessing both hydrophilic and hydrophobic properties. An amphiphilic molecule has a polar water-soluble group attached to a water-insoluble hydrocarbon chain of any kind, including methyl groups or typically $CH_3(CH_2)_n$ chains, with $n \geq 1$, preferably $\geq 3$. The amphiphilic nature of the condensable monomer is substantially given by the highly polar, hydrophilic $R_1$ to $R_3$ groups, which are preferably —OH groups, and the hydrophobic "tail" composed of the R group, which in some preferred embodiments consists of unsubstituted or substituted aliphatic moieties, saturated or not, such as e.g. alkyl, allyl, vinyl, alkynyl, phenyl, benzyl, cycloalkyl, hydroxyl, carboxyl, amino or thiol groups.

Once added to the biphasic solution, the monomeric precursors concentrate at the interface of said solution due to their very amphiphilic nature. Each of the three polar condensable groups in a precursor molecule, facilitated by water molecules, forms a hydrogen bond to a nearby condensable group of another precursor molecule. Over a suitable period of time, the tetrahedral monomer molecules form a regular network of hexagonal grids through the hydrogen bonds. Over another suitable period of time, a condensation process takes place, wherein two hydrogen-bond connected condensable groups are bond covalently by releasing one $H_2O$ molecule. One of the most used condensable groups is the OH group, which can be produced through hydrolysis from a hydrolizable precursor. The hydrolysis process can be performed prior to or simultaneously with the condensation process.

In a particular aspect, the method further comprises the addition of a catalyst to the biphasic solution. Even if not strictly necessary, the method according to the present disclosure can take advantage of the use of a catalyst to enhance or expedite the chemical reactions needed to produce the polymeric structures of the invention. The term "catalyst" refers herein to any substance which allows the increase in the rate of a chemical reaction of one or more reactants. In the presently disclosed method, such catalysts are in particular useful for driving the cross-linking reactions between oxygen atoms of different metal or metalloid oxides monomer precursors, said reaction being needed for the formation of covalent bonds between monomers and therefore for the formation of the monolayer shell structure. Any suitable catalyst can be exploited for that purpose such as a base, an acid, an organic salt, an inorganic salt, amino acids, polypeptides, enzymes, or any combination thereof. Catalysts can be for instance ammonium hydroxide or inorganic or organic compounds containing tin, bismuth, titanium, zirconium, platinum, and/or amines.

The polymerization process proceeds for at least one hour up to several days, depending on several factors such as temperature, the presence of a catalyst and so forth.

In some embodiments, the aqueous solution or the organic phase of the biphasic solution can comprise an active agent as previously described.

The method can also comprise a further step of heating the biphasic solution for a suitable period of time after the formation of the hydrogen-bonded monomer precursor condensed layer. The heating generally accelerate the cross-linking reaction of the monomers and the formation of the covalent-bonded metal- or metalloid-oxide polymeric structure. In a particular aspect, the biphasic solution is heated at a temperature between 40° C. and 99° C., preferably at a temperature between 65° C. and 85° C.

Additionally, the method comprises a last step of removing the R group and replacing it through any suitable method before or after a possible purification step of the final polymeric structure. For example, it is possible to remove the R group through a strong oxidizing agent such as a mixture of $H_2O_2$ and $H_2SO_4$ in a suitable ratio, leaving an OH group in the place of R. It is also possible to reduce the OH group into a H group using a suitable reducing agent known in the art.

Similar to the flat polymeric structures, a method for producing the hollow micro- or nanostructure as previously described is herein disclosed. Said method is quite close to the previous one, and is characterized in that it comprises the following step:

a) Providing a water-in-oil or an oil-in-water emulsion comprising a surfactant;

b) adding to said emulsion amphiphilic condensable monomer precursors of the formula:

wherein

X is a metal or metalloid element selected from the group consisting of Si, Ge, and Sn, $R_1$, $R_2$ and $R_3$ are the same or different condensable moieties and R is a non-polar organic moiety;

c) allowing the deposition and condensation of the monomer precursors on the aqueous solution-organic phase interfaces of the emulsion droplets; and d) allowing the polymerization process to proceed for a suitable period of time.

The R groups of the monomer precursors according to this method have the same features of the precursors already described for the flat polymeric structure production method. Different R groups can be selected in order to e.g. improve, ameliorate or accelerate the chemical reactions of the present method, enhance the yield of the final products, reduce the costs of the starting materials and so forth. The choice of the R non-polar, hydrophobic organic moiety present in the monomer precursors is particularly useful in at least some steps of the present method, because said precursors can e.g. compete to a surfactant for the polar phase of the emulsion, thus allowing the formation of a regular array of metal- or metalloid-oxide monomers around the emulsion droplets. Particularly suitable hydrophobic moieties are for instance unsubstituted or substituted aliphatic moieties, saturated or not, such as e.g. alkyl, allyl, vinyl, alkynyl, phenyl, benzyl, cycloalkyl, hydroxyl, carboxyl, amino or thiol groups. For example, halo-substituted hydrocarbons such as fluorocarbon chains (e.g., perfluoroalkanes) are suitable hydrophobic moieties when e.g. the nonpolar phase is a fluorocarbon fluid such as perfluorooctane. The functional groups can be either included in the micro-nanocapsules obtained by the method of the invention, or can be removed later on with any suitable means, as long as the obtained micro-nanocapsules maintain their physico-chemical properties.

In the frame of the present disclosure, an "emulsion" is a mixture of two or more fluids that are normally immiscible (unblendable). Emulsions are part of a more general class of systems of matter called colloids. Although the terms colloid and emulsion are sometimes used interchangeably, in the frame of the present disclosure the term emulsion is used when both the dispersed and the continuous phase are fluids, such as e.g. liquids. In an emulsion, one fluid (the "dispersed phase") is dispersed in the other (the "continuous phase") in the form of droplets. Preferred emulsions according to the present invention are microemulsions or nanoemulsions, i.e. emulsions in which the droplets of the dispersed phase are micro- or nanometer sized.

In the frame of the present disclosure, a "surfactant" is any substance which lowers the surface tension of the medium in which it is dissolved, and/or the interfacial tension with other phases, and, accordingly, is positively adsorbed at the liquid/vapour and/or at other interfaces. The term surfactant is also applied correctly to sparingly soluble substances, which lower the surface tension of a liquid by spreading spontaneously over its surface. It includes soaps, detergents, syndets, emulsifiers and the like. Particularly suitable surfactants according to the present disclosure are polyoxyethylene nonylphenyl ether and glycolic acid ethoxylate lauryl ether.

Any type of dispersing means are intended to be included in the present method, as long as it is suitable for permitting the formation of an emulsion. Such dispersing means are for instance stirring, ultrasonication and/or shaking.

The method exploits the molecular competition for the polar phase of the emulsion between the metal- or metalloid-oxide monomer precursors and the surfactant. Once few metal- or metalloid-oxides precursor molecules are anchored at the polar solution-nonpolar solution interface within close proximity, strong hydrogen bonds form between the hydroxyl subgroups of adjacent monomers. In this way, the formation of a network of metal- or metalloid-oxides molecules, arranged in a regular array, is permitted. As such, the surfactant molecules have to compete with a network of hydrogen-bonded precursor molecules in order to come back to the interface, which in this case has become increasingly difficult and more improbable over time. This drives an almost unidirectional reaction towards the hydrogen-bonded, monolayer, metal- or metalloid-oxides monomer precursor shell formation. Preferably, the formation of the monolayer monomer shell is carried out for at least 18 hours at room temperature. This reaction is finished by carrying out the cross-linking reaction over a suitable period of time, in which covalent bonds form among the hydrogen-bonded monomers, resulting in a cross-linked metal- or metalloid-oxide monolayer shell. Such a time period can vary from one hour to several days, depending on the particular reaction conditions. For example, the presence of one or more catalyst in the emulsion can expedite the cross-linking reaction.

The method can also comprise a further step of heating the emulsion for a suitable period of time after the formation of the hydrogen-bonded monomer precursor shell, with or without the use of additional dispersing means. The heating generally accelerate the cross-linking reaction of the monomers and the formation of the covalent-bonded metal- or metalloid-oxide micro- or nanocapsule shell. In a particular aspect, the emulsion comprising metal- or metalloid-oxide precursor monomer shells is further heated for at least 2 hours at a temperature between 40° C. and 99° C., preferably at a temperature between 65° C. and 85° C., most preferably at 70° C. In a further preferred aspect, the emulsion comprising dispersed metal- or metalloid-oxide is heated at 70° C. for at least 2 hours under shaking or stirring.

Similar to the method for producing flat monolayer structures, a catalyst can be added in the aqueous phase, the organic phase or both, and said catalyst has the same characteristics of the ones already outlined above. Moreover, the method further envisages the possibility of including within the aqueous solution and/or the organic phase an active agent as the ones previously described.

In a particular aspect, the metal or metalloid oxide monomers used in the method of the present disclosure are functionalized. Any kind of molecular group can be attached or otherwise coupled to the metal or metalloid oxide monomer precursors to e.g. improve, ameliorate or accelerate the chemical reactions of the present method, enhance the yield of the final products, reduce the costs of the starting materials and so forth. In a particular aspect of the method of the present disclosure, the metal- or metalloid-oxide monomer precursors have a hydrophobic moiety attached thereto. This is particularly useful in at least some steps of the present method, because monomers functionalized with hydrophobic moieties can e.g. compete with the surfactant for the polar phase of the emulsion, thus allowing the formation of a regular array of metal- or metalloid-oxide monomers around the emulsion droplets. Particularly suitable hydrophobic moieties are for instance unsubstituted or substituted aliphatic moieties such as e.g. alkyl, allyl, vinyl, alkynyl, phenyl, benzyl, cycloalkyl, hydroxyl, carboxyl, amino or thiol groups. Fluorocarbon chains such as perfluoroalkanes are another suitable hydrophobic moiety when e.g. the nonpolar phase is a fluorocarbon fluid such as perfluorooctane. The functional groups can be either included in the micro-nanocapsules obtained by the method of the invention, or can be removed later on with any suitable means, as long as the obtained micro-nanocapsules maintain their physico-chemical properties.

In one aspect, some of the steps of the method of the present disclosure can be performed in a different order compared to the general, above-disclosed method. For instance, instead of adding a metal- or metalloid-oxide monomer precursor to a previously-prepared polar-nonpolar emulsion comprising a surfactant, such monomer precursor can also be added to the non-polar only solution comprising a surfactant, to which a polar solution is later added. If needed, cross-linking catalysts can be added to the solutions at any time. An elevated reaction temperature can also be used. Any variation of the method is intended to be included in the present disclosure, as long as it is suitable for the formation of the micro- or nanocapsules of the present invention. The same is applicable to the flat polymeric structures according to the invention, as will be evident for a person skilled in the art.

A specific embodiment of the invention relies in a method to prepare trisilanol monomer precursors containing no hydrochloride by-product for making $SiO_2$ micro- or nanocapsules, the method comprising the steps of: 1) homogeneously disperse no more than 0.15% by volume of water in a mixture consisting of no less than 30% by volume of a low-boiling temperature, polar aprotic or protic organic solvent, no less than 3% by volume of a fatty alcohol, and a nonpolar solvent for the rest of the volume; 2) dissolve an organotrichlorosilane in a molar amount of three times as much the molar amount of the said water content in 1 mL of the said nonpolar solvent; 3) disperse the later mixture to the former mixture and let the reaction proceed for at least 10 seconds; 4) heat the mixture solution near the boiling temperature for at least 30 minutes to remove the hydrochloride by-product and the low-boiling temperature polar organic solvent. Suitable polar aprotic or protic organic solvents are for example acetone, methanol, ethanol and the like; suitable fatty alcohol are for example hexanol, heptanol and the like; suitable organotrichlorosilanes are for example octyltrichlorosilane, octenyltrichlorosilane, octadecyltrichlorosilane and the like.

One aspect of the invention relates to compositions comprising the monolayer flat membrane and/or the hollow micro- or nanostructures as disclosed above. The composition may, optionally, comprise further molecules capable of altering the characteristics of the structures of the invention thereby, for example, reducing, stabilizing, delaying, modulating and/or activating the function thereof. The composition may be in solid or in fluid form, and may be, inter alia, in the form of powder, tablet, solution, aerosol or gel/hydrogel.

Flat monolayer polymeric structures, micro- nanostructures such as nanocapsules and a composition according to the invention can be used for many purposes. For instance, when functionalized on one side of the monolayer shell, micro- and nanocapsules comprised in a composition can be useful for removing or sequestering target compounds from an environment, especially aqueous ones. In many instances, it is necessary to remove e.g. toxic or pollutant compounds from environments such as drinking water, food, biological fluids, industrial effluents and public waste water, and radioactive waste. Polymeric structures, micro- nanostructures and/or compositions of the invention can be placed in contact with the environment in an amount sufficient to bind the target compounds, and are then removed or separated from the environment, leaving the environment substantially free of the said target compounds. Additionally, all these products can be used as molecular size-selective transport membrane or even ion-selective transport membrane, encapsulation of chemical compounds or active agents, as a coating in e.g. flexible electronics and the like.

Further, a composition comprising the structures of the invention can be used for diagnosis, treatment or prophylaxis of diseases in an animal, in particular a mammal and more particularly a human being.

A person skilled in the art will appreciate that the structures or compositions according to the present invention can comprise for example micro- and/or nanocapsules comprising a shell monolayer having a single metal- or metalloid-oxide species, several metal- or metalloid-oxide species, or any combination of micro- and/or nanocapsules comprising a shell comprising a monolayer of one or more metal- or metalloid-oxide species. For example, a composition can comprise nanocapsules comprising a monolayer shell comprising $SiO_2$, or comprising a mixture of e.g. $SiO_2$ and $SnO_2$ on the same nanocapsules' monolayer shell, or a composition can comprise nanocapsules having a monolayer shell comprising e.g. $SiO_2$ and microcapsules having a monolayer shell comprising e.g. $SnO_2$, and so forth. Any suitable combination can be envisaged depending on specific needs. The same can be applied for the flat membrane structures.

A composition according to the present disclosure is also meant to include pharmaceutical compositions. In a particular aspect, therefore, the composition of the invention is a pharmaceutical composition optionally further comprising a pharmaceutically acceptable carrier, excipient and/or diluent.

In the frame of the present disclosure, the term "pharmaceutical composition" relates to a composition for administration to a patient, preferably a human patient. The pharmaceutical composition of the invention comprises the micro- and/or nanostructures and/or the flat membrane polymeric structures as disclosed above. The pharmaceutical composition of the present invention may, optionally and additionally, comprise a pharmaceutically acceptable carrier. By "pharmaceutically acceptable carrier" is meant a non-toxic solid, semisolid or liquid filler, diluent, encapsulating material or formulation auxiliary of any type. Examples of suitable pharmaceutical carriers are well known in the art and include sodium chloride solutions, phosphate buffered sodium chloride solutions, water, emulsions, such as oil/water emulsions, various types of wetting agents, sterile solutions, organic solvents etc. Preferably the carrier is a parenteral carrier, more preferably a solution that is isotonic with the blood of the recipient. The carrier suitably contains minor amounts of additives such as substances that enhance isotonicity and chemical stability. Such materials are non-toxic to recipients at the dosages and concentrations employed, and include buffers such as e.g. phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

Compositions comprising such carriers can be formulated by well-known conventional methods. Generally, the formulations are prepared by contacting the components of the pharmaceutical composition uniformly and intimately with liquid carriers or finely divided solid carriers or both. Then, if necessary, the product is shaped into the desired formulation. The pharmaceutical composition may be in the form of spray, capsules, tablets, granules, syrup, emulsion, suppository, injection, ointment, tape and the like.

These pharmaceutical compositions can be administered to the subject at a suitable dose. The dosage regimen will be determined by the attending physician and clinical factors. The therapeutically effective amount for a given situation will readily be determined by routine experimentation and is within the skills and judgment of the ordinary clinician or physician. The pharmaceutical composition may be for administration once or for a regular administration over a prolonged period of time. Administration of pharmaceutical compositions of the invention may be effected by different ways, e.g., by intravenous, intraperitoneal, subcutaneous, intramuscular, intradermal, oral, intranasal or intrabronchial administration.

The components of the pharmaceutical composition ordinarily will be stored in unit or multi-dose containers, for example, sealed ampoules or vials, as an aqueous solution. Preservatives and/or other additives may also be present such as, for example, antimicrobials, anti-oxidants, chelating agents, inert gases and the like. The pharmaceutical composition may comprise further agents depending on the intended use of the pharmaceutical composition.

The pharmaceutical composition may be particularly useful for the treatment or prophylaxis of diseases. In particular, the pharmaceutical composition of the invention is useful in the prevention and/or treatment of any kind of cancer, including blood cancers, and infections such as bacterial, viral or fungal infections. For what concerns for example micro-nanocapsules comprised in the pharmaceutical compositions of the invention, due to the specific features of these structures, scarcely accessible body sites can be specifically and efficiently targeted and treated with little invasive means. Diseases such as cartilage, bone, kidney, lung, pancreas or brain diseases can be easily treated with the pharmaceutical compositions of the invention. Micro-nanocapsules comprised in the pharmaceutical compositions can e.g. be used as drug carriers for the treatment or prophylaxis of diseases including but not limited to an autoimmune disease or a neurodegenerative disease, for example, rheumatoid arthritis, Systemic Lupus Erythematosus (SLE), antiphospholipid syndrome, immune thrombocytopenia (ITP)1, Kawasaki disease, Guillain-Barr syndrome (GBS), multiple sclerosis (MS), chronic inflammatory demyelinating polyneuropathy (CIDP), Alzheimer's Disease, Parkinson's Disease, psoriasis; bacterial infections including but not limited to Bacterial Meningitis, Cholera, Diphtheria, Listeriosis, Pertussis (Whooping Cough), Pneumococcal pneumonia, Salmonellosis, Tetanus, Typhus, Tuberculosis or Urinary Tract Infections; viral infections, including but not limited to Mononucleosis, AIDS, Chickenpox, Cytomegalovirus Infection, Dengue fever, Ebola Haemorrhagic fever, Hand-foot and mouth disease, Hepatitis, Influenza, Mumps, Poliomyelitis, Rabies, Smallpox, Viral encephalitis, Viral gastroenteritis, Viral encephalitis, Viral meningitis, Viral pneumonia or Yellow fever; fungal infections including but not limited to Aspergillosis, Blastomycosis, Candidiasis, Coccidioidomycosis, Cryptococcosis, Histoplasmosis or Tinea pedis.

The polymeric structures of the invention comprised in the pharmaceutical compositions can be also useful as gene-delivering agents. For example, natural and/or modified nucleic acids can be loaded in the inner core of the micro-nanocapsules of the pharmaceutical composition and targeted to e.g. specific body sites depending on patients' needs. Micro-nanocapsules comprised in the pharmaceutical compositions can enter inside a contacted target cell by e.g. endocytosis, phagocytosis or pinocytosis, possibly mediated by cell membrane proteins, and release the nucleic acid payload comprised in the inner core of the micro-nanocapsules after shell disruption by e.g. ultrasound administration. Due to the very characteristic physico-chemical features of the polymeric structures disclosed herein, it can also be envisaged the release of the nucleic acid payload after fusion of the micro-nanocapsules' shell with the cell membrane.

EXAMPLE 1

A new class of ultrathin, single-walled hollow silica nanocapsules have been developed, consisting of a fluid inner core and a monolayer of silica shell. Different from other polymer-based systems, silica nanocapsules disclosed herein are strong yet highly sensitive to external stimuli, and uniquely multifunctional. Analyses performed on the monolayer silica nanocapsules reveal striking mechanical properties and rich condense matter physics in such silica nanocapsules. They are impermeable to water molecules, strong to hold the integrity in vacuum, fragile to local flow shearing forces and ultrasound waves, and flexible and fusible like soap bubbles. In particular, their unique ultrasound fragility is particularly suitable in controlled drug delivery.

Figure 1:
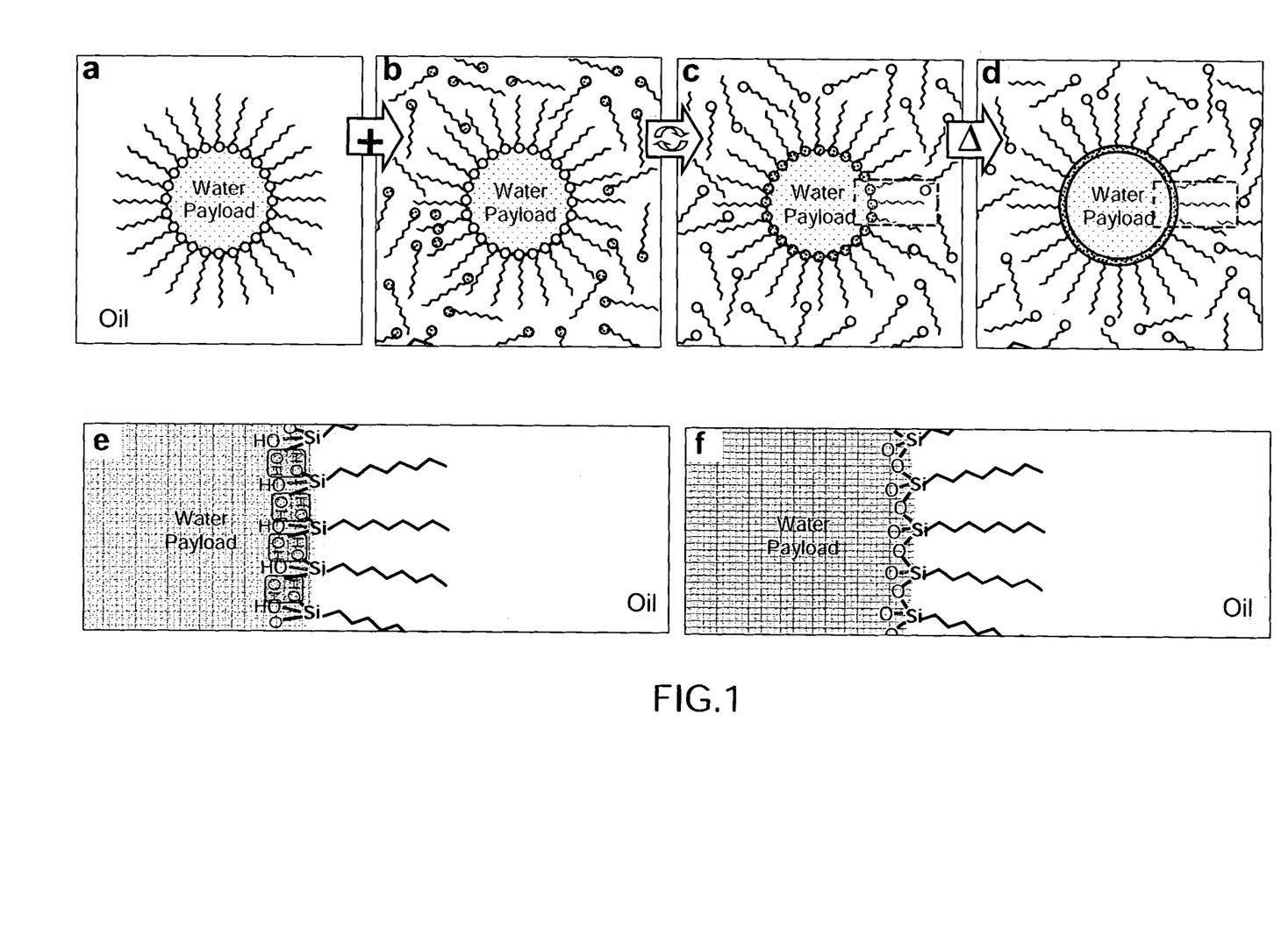
FIG. 1 depicts the principle of the self-assembly for single-walled nanocapsules.

The principle of self-assembly for the synthesis is illustrated in FIG. 1. In the first step (FIG. 1a), a water-in-oil nanoemulsion system is formed by dispersing a pre-calculated amount of water containing ammonium hydroxide as a cross-linking catalyst with possibly payload content (the water phase) into a nonpolar solvent (the oil phase) with the assistance of a surfactant. In the second step (FIG. 1b), hydrolyzable trichlorosilane, with one long alkyl chain is added ("+") into the nanoemulsion system, where a quick hydrolysis reaction takes place and converts the silane molecules into trisilanol, the monomer precursor for $SiO_2$. In the third step (FIG. 1c), the system of the trisilanol monomers and the nanoemulsion reacts for a sufficient period of time, wherein the trisilanol molecules replaces the surfactant molecules and attaches to the surface of the water droplets. Adjacent trisilanol molecules are bonded to each other through hydrogen bonds. In the fourth step (FIG. 1d), a mild heating ("Δ") is applied to the trisilanol-wrapped nanoemulsion system, accelerating the condensation reaction to form a silica, or more generally, polysiloxane, shell. FIGS. 1e and f show the detailed molecular structures corresponding to the dashed rectangle regions in FIGS. 1c and d, respectively.

The principle of direct molecular assembly on the surface of liquid droplet is vastly different from previous techniques for monolayers and nanocapsules. Two key factors ensure the progress of the self-assembly reaction as outlined above: first, the trisilanol functional group contains three tightly packed, highly polar Si—OH subgroups and is thus strongly hydrophilic. Extended Hückel calculations (data not shown) using commercial computational chemistry software show that the polarity of the trisilanol group is comparable to most surfactants. Therefore in an emulsion system the trisilanol molecules are able to compete with the surfactant. Second, once two or more of the trisilanol molecules are anchored at the water-oil interface within close proximity, strong hydrogen bonds form between the hydroxyl subgroups (FIG. 1e). The triple hydroxyl groups enable the formation of a network of trisilanol molecules arranged in a regular array. As such, the surfactant molecules now have to compete with a network of hydrogen-bonded trisilanol molecules in order to come back to the interface, which has become much more difficult. The overall reaction, therefore, favours the forward direction over the reverse. Furthermore, the steric repulsion in the long alkyl tail ensures that the trisilanol is always oriented normal to the water-oil interface and prohibits the deposition of additional layers. FIG. 1g shows the three-dimensional molecular structure of the silica monolayer membrane, the top-view of which is shown in FIG. 1h where the hexagonal structure is clearly depicted. In the illustration the small local curvature is ignored. Based on the Si—O bond length of 1.64 Å and taking into account the tetrahedral angle, the side of each hexagon element is 3.08 Å, which is much larger than the 1.42 Å in graphene. The bond angles play a key role in the properties of the membrane. Similar to carbon, the four sigma bonds of the silicon atom forms a tetrahedron with a rigid bond angle of 109.5° (FIG. 1i). The Si—O—Si bond angle possesses a high degree of bending flexibility, ranging from 120° to 180° with equilibrium at 142°. This results in a highly flexible silica membrane that is almost flat at equilibrium, enabling capsules in the size range of 10 nm-1000 nm with little van der Waals strain. Therefore, the membrane can be considered as a "soft" two-dimensional crystal. Furthermore, the molecular flexibility also ensures that the size of the silica capsules follows that of the droplet defined by the surfactants, providing great size tunability.

Silica nanocapsules with two types of surfaces have been synthesized: a hydrophobic-type with octadecyl (C18) group on the surface, and a hydrophilic-type with octyl (C8) group on the surface (see Methods). In the synthesis, cyclohexane has been used as the nonpolar (oil) phase, with ionic and non-ionic surfactants for the C18- and C8-capsules, respectively. The experimental results demonstrate the generality and the flexibility of the principle. These are the first demonstration of covalent-bonded, soft, single-walled crystalline membrane directly assembled onto the surface of liquid droplets.

Figure 2:
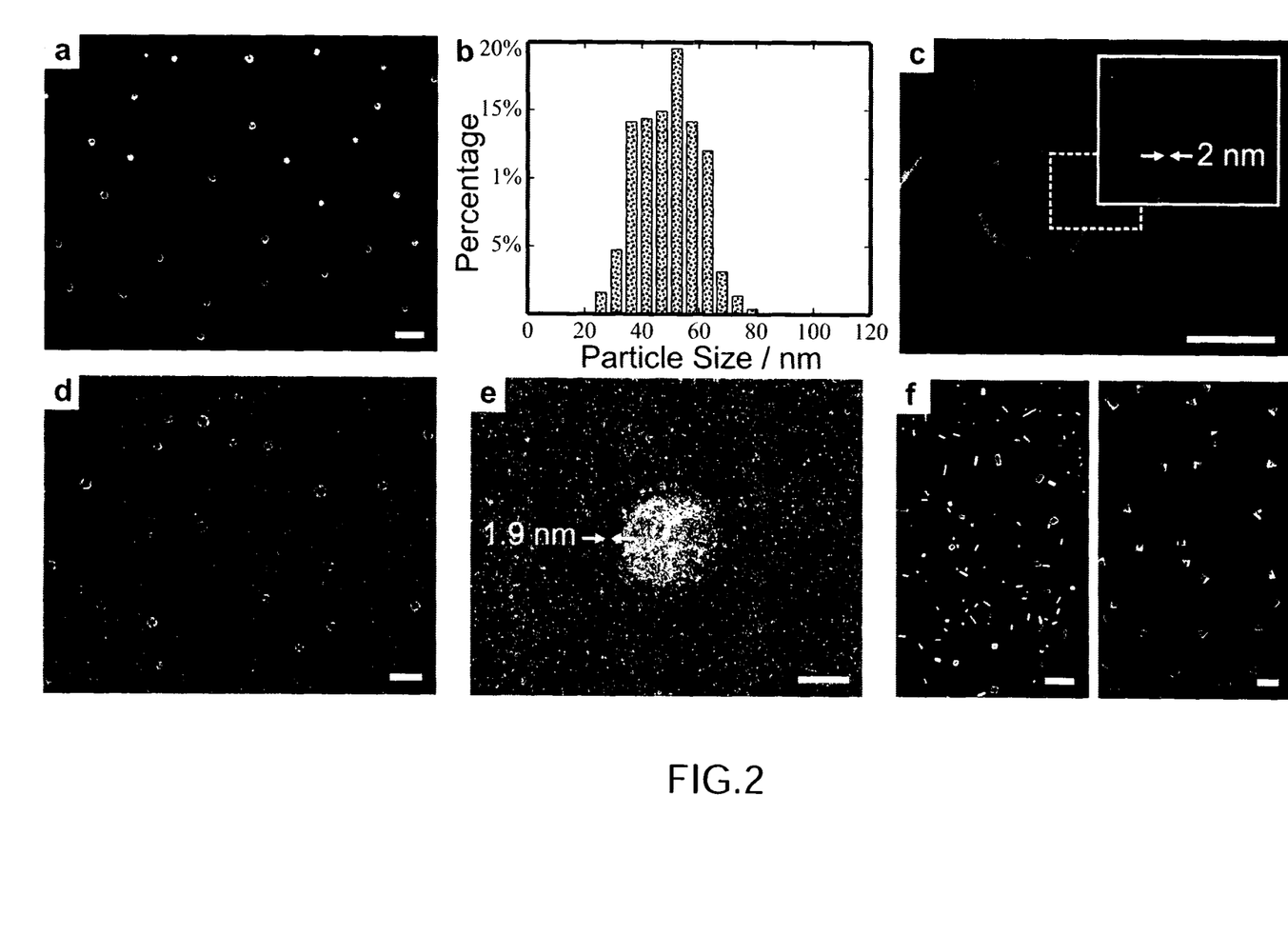
FIG. 2 depicts the results of the nanocapsules synthesis.

FIG. 2a shows a typical scanning electron microscopy (SEM) image of the C18-silica capsules synthesized using ionic surfactant glycolic acid ethoxylate lauryl ether as the emulsifier and octadecyltrichlorosilane as the self-assembly component. The capsules were loaded with 50 mM calcein, although a significant fraction of the fluorescent dye molecules were lost during the synthesis due to their affinity to the surfactant. The synthesis product was purified with dialysis, and the presence of calcein in the capsules was confirmed using a fluorescence spectrum measurement (data not shown). The capsules were nearly spherical with a small degree of deviation due to the interaction of the calcein molecules with the surfactant and the trisilanol molecules. The capsules were strong to maintain their integrity in vacuum without rupture but vulnerable to electron beam radiation under large magnification. The vulnerability to electron beam is dependent on the length of the surface alkyl chains, with the C18-type slightly stronger than the C8-type.

FIG. 2b shows the size distribution of the capsules obtained from 350 particles. The mean value of the diameter was 50 nm, with a standard deviation of 15 nm. To measure the thickness of the silica shell, s synthesis reaction has been performed, with reduced amount of silane such that the trisilanol was insufficient to cover the droplets. This caused a sharply reduced yield of capsules and only occasional incompletely covered capsules could be identified under SEM (FIG. 2c).

The shell thickness, measured from the SEM images of an incompletely formed capsule, was 2 nm, which was at the resolution limit of the available electron microscope. The measured thickness matches the theoretic length of one octadecyltrisilanol molecule (2.30 nm) well, clearly indicating that the shell was single-walled. An EDX measurement (data not shown) reveals that the capsules retain water in the vacuum, suggesting an impermeable shell membrane.

FIG. 2d shows a typical SEM image of the C8-silica capsules synthesized using non-ionic surfactant polyoxyethylene nonylphenyl ether as the emulsifier and octyltrichlorosilane as the self-assembly component. The capsules were loaded with 0.1M $CuCl_2$, which coordinated with ammonia and became dark blue after excessive ammonium hydroxide addition. During the synthesis, a significant fraction of the copper ions were again lost to the surfactant. The synthesis product was purified through multiple dialyses. The capsules were almost perfectly spherical owing to the absence of interference at the interface. Like the C18 counterpart, the C8-capsules were also strong in vacuum without rupture. However, they show less contrast under SEM imaging and are more vulnerable to electron beam radiation. The vulnerability to electron beam prohibited the measurement of the shell thickness using SEM. The inventors thus performed transmission electron microscopy (TEM) imaging with uranyl salt negative staining to assist the identification and the measurement of the capsules.

FIG. 2e shows a typical TEM image where the shell membrane appeared as a dark circle formed by the deposition of uranium ions on the outer surface of the capsule. The shell membrane thickness, measured from several TEM images, was 1.9 nm. This was slightly larger than the theoretic molecular length of the octyltrisilanol molecule (1.14 nm) due to the uranyl ion deposit. It is nonetheless still a clear evidence for single-walled shell membrane. Moreover, the lighter internal region of the capsule compared with the outer region suggests that the capsule membrane is impermeable to uranyl ions.

Interface activities play a vital role in the formation of the capsules. To demonstrate this, capsules loaded with 1 mM fluorescein dye molecules have been synthesized. Because fluorescein has less carboxyl group (one) than calcein has (four), the former is much more amphiphilic than the latter and causes greatly promoted disturbances at the water-oil interface, as shown in FIG. 2f. The left panel shows a typical SEM image of the product using glycolic acid ethoxylate lauryl ether as the surfactant. A significant fraction of the capsules became rods and cubs. The right panel shows a typical SEM image of the capsules produced using polyoxyethylene nonylphenyl ether for surfactant. A large portion of the capsules became tetrahedrons, while rods and cubes are also found. Further tests indicated that these structures are subject to a vulnerability to the electron beam irradiation similar to the spherical capsules, suggesting a hollow interior. Such a mechanism can serve as the basis for shape control.

Figure 3:
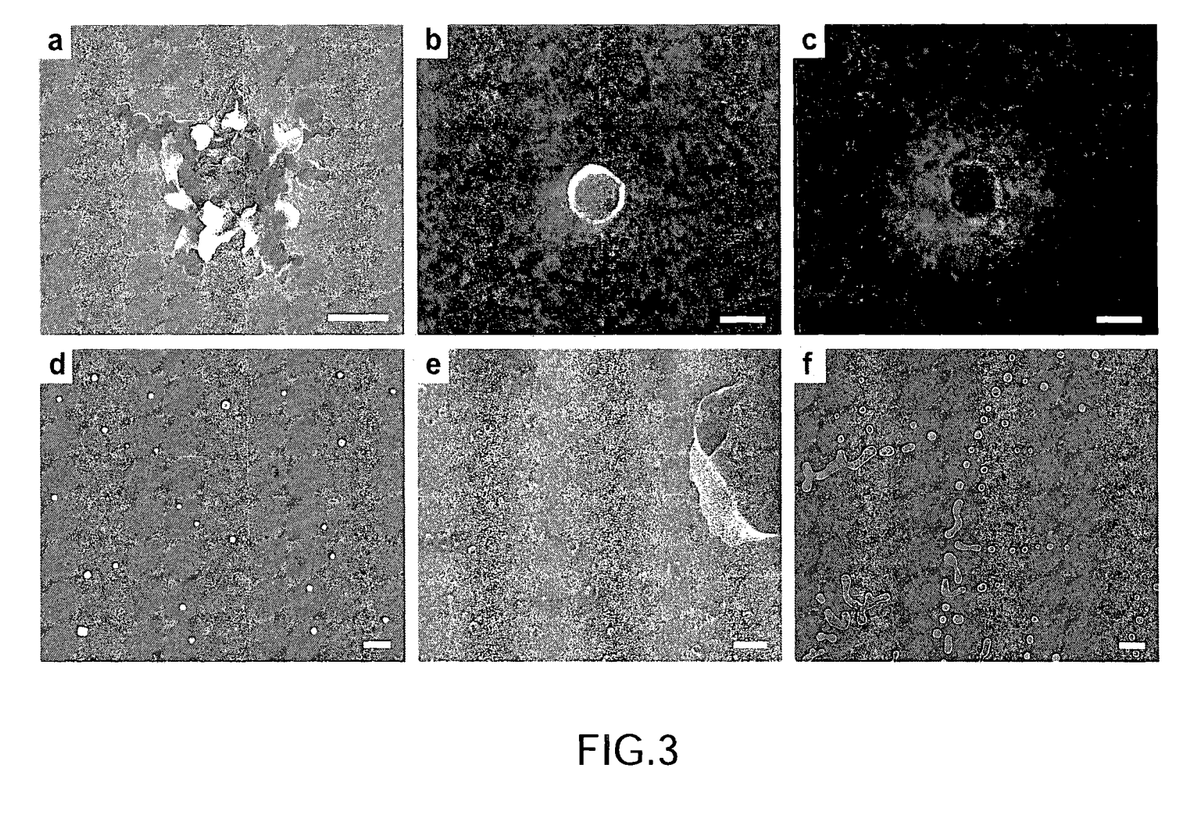
FIG. 3 depicts the mechanical properties of the monolayer membrane of nanocapsules.

The strong yet flexible Si—O bond results in unique mechanical properties of the membrane and a rich range of condensed matter physics phenomena. While the capsules are strong against vacuum, they are fragile to external local shear stress. FIG. 3a shows the SEM image of a cluster of C18-capsule residues after being ruptured by ethanol. Here the capsules were first transferred from cyclohexane to ethanol, after which a 10-μL drop was placed and dried on a silicon substrate. While the capsules were pulled together while the ethanol is evaporating, the strong local shear due to the fast drying induced ruptures in nearly 100% of the capsules.

The capsules are also prone to damage under electron beam irradiation. FIGS. 3b and c shows the SEM image of a C18-capsule before and after electron beam induced rupture, respectively, in two consecutive scans at a gun setting of 10 kV and 10 µA. The rupture is probably due to the heat generated by the electron beam bombardment.

More importantly, the capsules are fragile to ultrasound waves. FIGS. 3d and e displays the SEM image from the same C18-capsule solution before and after being irradiated by a 44 kHz ultrasound wave for one minute at an intensity of approximately 0.4 W/cm2. This fragility to ultrasound waves is of direct practical value applications of ultrasound mediated drug delivery and release.

The very flexible capsule membrane also leads to striking fusing behaviour. FIG. 3f captures such fusing action of C8-capsules in SEM. The C8-capsules were purified with four times of dialysis at ratio of 1:1000 to sufficiently remove the surfactant for unambiguous image interpretation. As the drop of the water solution containing the capsules were drying on a silicon substrate, the capsules were pulled by the water into tighter and tighter space. At certain point the capsules start to fuse into each other and form larger structures. This is similar to what can be found in soap bubbles, although the membrane involved is a covalently bonded, crystalline film. The behaviour also bears similarity to cell plasma membranes.

The synthesis reaction involves quite harsh condition in terms of the pH. The trichlorosilane releases a significant amount of HCl during the hydrolysis step, which preferentially enters the tiny water droplets, causing a drastic reduction of pH, causing a deviation from the optimal condition for later condensation step. The HCl by-product cannot be neutralized outside the water droplets in the oil phase, since acid-base reaction does not take place in nonpolar solvents. Although excessive ammonium hydroxide was used to avoid this, the internal pH of the capsules was rendered highly basic. On the other hand, protein encapsulation using this technique requires near-neutral internal pH to avoid denaturation. Thus a pre-hydrolyzation step is preferable, where trisilanol is prepared and the HCl by-product is eliminated beforehand. To avoid the simultaneous (albeit slower) condensation, a pre-hydrolyzation at low silane concentration in a nonpolar solvent (cyclohexane) with precisely controlled amount of water has been performed (see Methods below). The water was dispersed at the molecular level (no droplets) with the assistants of a polar non-protic solvent (acetone) and a fatty alcohol (1-heptanol). The HCl by-product was removed by heating the solution following the completion of the hydrolysis. As such the pre-hydrolyzed trisilanol solution is stable without appreciable condensation for several months.

Synthesis experiments (data not shown) indicate an equivalency of the pre-hydrolyzed trisilanol to the direct use of trichlorosilane except the absence of HCl production. In addition, it has been also tested metal-catalyzed condensation without ammonia and the final heating step. Initial results (data not shown) using zinc acetate as a catalyst suggest good promise. With these techniques proteins like the insulin, growth factors, antibodies, and vaccines can be encapsulated. To achieve capsules with true atomically thin membrane, the alkyl chain can be removed through selective Si—C bond cleavage. Tunable thickness is enabled through additional condensation of tetraethoxysilane on top of the silica membrane. Following the same principle, a number of other tetravalent systems, such as Ge and Sn, can also be utilized for capsule fabrications. With certain modifications, the principle can also be used in the synthesis of nanocapsules with nonpolar (oil) content. Functionalization of the capsule surface can be achieved by choosing a silane with vinyl group at the distant end of the alkyl chain, where the double-bond terminal provides an anchor for attaching a variety of functional groups. Adding one more layer of silane with amine group also serves the purpose well. Furthermore, the fusing property suggests that the single-walled silica membrane can behave quite similarly as lipid bilayers.

Methods

Chemicals. All chemicals were used as purchased. Cyclohexane (HPLC-grade) was obtained from AppliChem. Polyoxyethylene (12) nonylphenyl ether (IGEPAL CO-720, average Mw 749) and glycolic acid ethoxylate lauryl ether (average Mw 360) were obtained from Aldrich. Octadecyltrichlorosilane (99.0%) was purchased from Fluka. n-Octyltrichlorosilane (97%) was purchased from Alfa Aesar. Ammonium hydroxide (28%) was obtained from Alfa Aesar. Fluorescein (free acid, 98%) was obtained from Aldrich. Calcein was obtained from Sigma. Copper chloride (97%) was purchased from Aldrich. Milli-Q water was used in all synthesis and purification work.

Preparation of the water phase. For water-only capsules, 28% $NH_4OH$ stock solution was used as the water phase. For $Cu^{2+}$-loaded capsules, 100 µL 0.1 M $CuCl_2$ solution was mixed with 900 µL $NH_4OH$ stock solution. The solution became dark blue due to the formation of copper-ammonia complex. For calcein-loaded capsules, 31 mg calcein was dissolved in 1 mL $NH_4OH$ stock solution. These water phase solutions were prepared fresh before the synthesis.

Preparation of trisilanol stock solution. The trisilanol stock solution was prepared in a strictly controlled hydrolysis reaction. In a 16-mL glass vial, 10 mL cyclohexane, 3 mL acetone, 400 µL 1-heptanol, and 20 µL of water were mixed and the mixture was treated in a ultrasonication bath for one minute to ensure sufficient solubilization of the water. For C18-trisilanol, 854 µL cyclohexane and 146 µL octadecyltrichlorosilane were mixed in a 1.5 mL eppendorf tube. For C8-trisilanol, 912 µL and 88 µL octyltrichlorosilane were mixed in a 1.5 mL eppendorf tube. Under rapid stirring, the silane solution (1 mL) was added to the cyclohexane mixture drop wise, resulting in a transparent solution. The mixture was allowed to react for 10 minutes under stirring followed by two hours of heating at 80° C. without cap in a fume hood. Cyclohexane was replenished when the fluid level is below 10 mL mark. The heating removes both the hydrochloride by-product and the acetone. After the heating step, the solution was allowed to cool. The 10 mL trisilanol stock solution appeared clear and indicated a pH of 5-6 on a pH stripe. Visible precipitations generally indicate premature silanol condensation. The resulting trisilanol concentration of the stock solution is 38 µM. The stock solution can be stored for several months without visible change in appearance.

Synthesis of silica nanocapsules. All synthesis was conducted in 6-mL glass vials. Typically, 200 µL surfactant (polyoxyethylene nonylphenyl ether or glycolic acid ethoxylate lauryl ether) was added into 5 mL cyclohexane (the organic phase). The mixture was briefly stirred with a magnetic stir bar. Subsequently, 100 µL of the water phase with payload was added into the organic phase under rapid stirring. 50 µL of silane (octadecyltrichlorosilane for C18-silica capsules, or octyltrichlorosilane for C8-silica capsules) was then added into the emulsion under rapid stirring. A nitrogen gun was used to gently blow the hydrochloride gas released in the reaction out of the vial. The vial was then tightly capped and the mixture was left being stirred in room temperature for at least 18 hours followed by at least two hours of heating at 70° C. under stirring.

Product purification. The nanocapsule product can be isolated from the rest of the mixture in two ways: dialysis or centrifugation. While dialysis is slower but works for both C8- and C18-type capsules with higher performance, centrifugation is faster but works only for C18-type capsules with less complete isolation. In the dialysis method, 1.4 mL solution from the synthesis was collected into a plastic eppendorf tube and mixed with 100 μL 1-heptanol. The mixture was centrifuged at 1000×g for five minutes. The supernatant was then removed and the sediment was redispersed in ethanol. The ethanol solution was subsequently diluted with water to 3 mL and transferred into a dialysis tube (molecular weight cut off 50 kDa). After three passes of dialysis against 2.5 L water, the purified product was collected into a glass vial. In the centrifugation method, the mixture was centrifuged at 1000×g for five minutes. The supernatant was then removed and the sediment was redispersed in ethanol.

EXAMPLE 2

In a similar approach planar single layered silica membranes have been also fabricated. Similar to the previous example, a biphasic system is employed to fabricate the membrane at the water-oil interface. In this fabrication, the two phases remain two separated layers due to their immiscibility and the gravity, and no surfactant is involved. The typical preparation procedure involves: 1) prepare a mixture of 2 mL water and 1 mL 28% ammonia in a 6-mL vial; 2) slowly and steadily add 3 mL cyclohexane without inducing mixing; 3) add 10 pL octyltrichlorosilane into the top cyclohexane layer; 4) let the reaction proceed in still for at least 18 hours; 5) heat the system at 70° C. for at least two hours in still without stirring; 6) remove unreacted octyltrichlorosilane by repeatedly removing and refilling the top cyclohexane layer slowly and steadily for at least five times. After the procedure, an organosilica (i.e. polysiloxane) membrane is available separating the two liquid phases.

Figure 4:
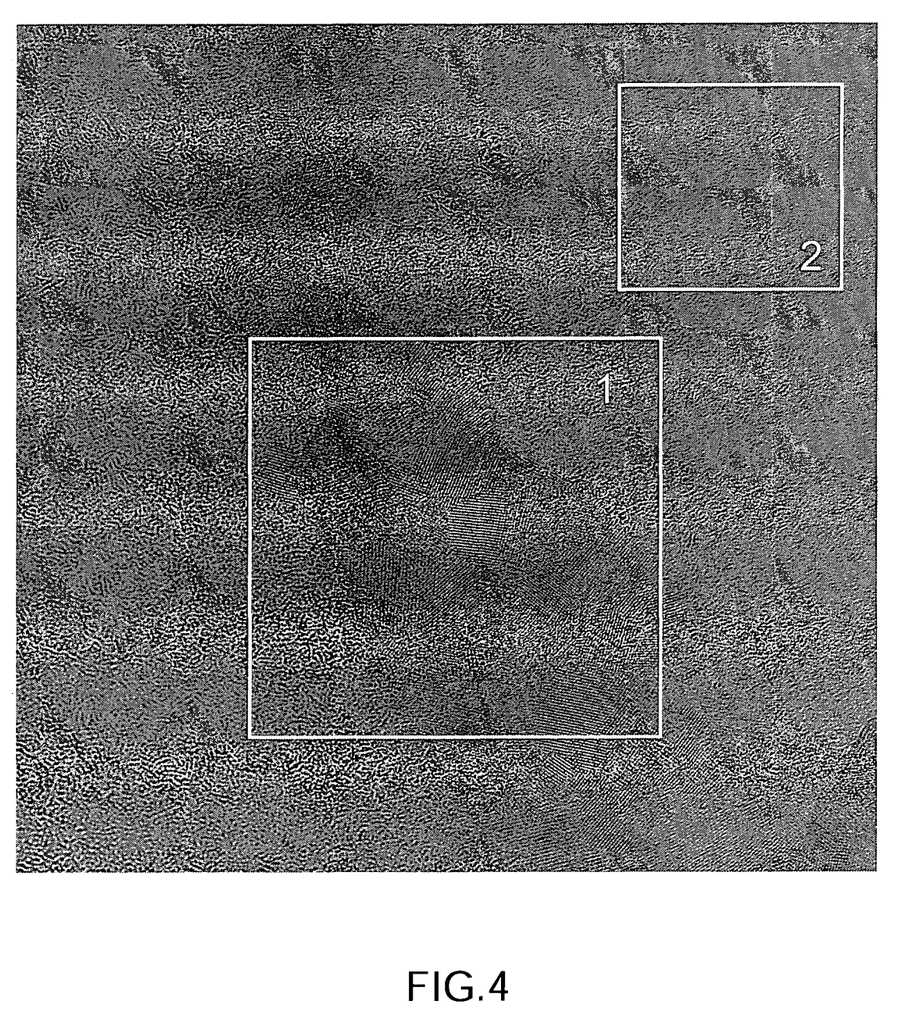
FIG. 4 shows a TEM image of the flat single layered membrane.

FIG. 4 shows a high-resolution TEM image of the single layer membrane picked up onto a holey carbon support (quantifoil). The atomic arrangement appeared to be amorphous in the region where there is only one layer of the fabricated membrane. However, in another region where folding occurs due to the high flexibility of the membrane and the sample preparation process, crystalline structures are clearly identified. In the single layer region (zone 2), the crystalline structure is transformed into amorphous appearance due to the random bundling of the surface alkyl groups, causing a random deviation of the Si atom from its original lattice. In the folded region (zone 1), on the other hand, the alkyl groups from the top and down layers can have a highly precise alignment due to the regular hexagonal grids, thereby forming alkyl pairs (one from the top layer and one from the down layer) that maintains the crystalline structures in certain specific directions.

The invention claimed is:

1. A polymeric structure comprising a substantially two-dimensional layer of covalently-bonded monomers of the formula:

wherein X is Si,
wherein X comprises a hydrophobic moiety comprising at least one carbon atom, wherein the hydrophobic moiety is configured to lie substantially perpendicularly compared to an Euclidean plane the X atoms lie on,
wherein the polymeric structure includes a substantially two-dimensional layer with a crystalline structure,
wherein the crystalline structure has a hexagonal lattice in which each of the hexagon vertices includes one X atom, and each of the hexagon edges comprises covalently bonded X-O-X atoms, and
wherein each of the hexagon lattices share a common edge having the covalently bonded X-O-X atom with a neighboring hexagon such that a flexible honeycomb structure of tessellated hexagons as the substantially two-dimensional layer is provided.

2. The polymeric structure of claim 1, wherein the X-0-X bond angle has a bending flexibility comprised between 120° and 180° with respect to the plane the X atoms lie on.

3. The polymeric structure of claim 1, wherein R further includes an active agent or is functionalized with an active agent.

4. A composition comprising the polymeric structure of claim 1.

5. A pharmaceutical composition comprising the polymeric structure of claim 1.

6. The polymeric structure of claim 1 for use in therapy, prophylaxis or diagnosis of diseases.

7. The polymeric structure of claim 1 for use as ion-selective transport membrane.

8. The polymeric structure of claim 1 for use as molecular size-selective transport membrane.

9. The polymeric structure of claim 1 for use as a coating.

10. The polymeric structure of claim 1 for use in encapsulation of chemical compounds or active agents.

11. The pharmaceutical composition of claim 5 for use in therapy, prophylaxis or diagnosis of diseases.

12. The polymeric structure of claim 2, wherein the X-O-X bond angle has an equilibrium at 142°.

13. The polymeric structure of claim 1, wherein the hexagonal lattice includes 6 X atoms at the six vertices of each hexagon.

14. The polymeric structure of claim 1, wherein the hydrophobic moiety incudes a fluorocarbon and/or a hydrocarbon.

15. The polymeric structure of claim 1, wherein the hydrophobic moiety includes a aliphatic moiety.

16. The polymeric structure of claim 3, wherein the active agent includes a hydrophilic agent.

* * * * *